United States Patent [19]

Gude et al.

[11] Patent Number: 4,547,578

[45] Date of Patent: Oct. 15, 1985

[54] PROCESS FOR REMOVING NAPHTHOQUINONE FROM PHTHALIC ANHYDRIDE PRODUCED THROUGH AIR OXIDATION OF NAPHTHALENE

[75] Inventors: Fritz Gude, Herne; Herbert Haferkorn, Bottrop, both of Fed. Rep. of Germany

[73] Assignee: Chemische Werke Huls Aktiengesellschaft, Marl, Fed. Rep. of Germany

[21] Appl. No.: 583,230

[22] Filed: Feb. 24, 1984

[30] Foreign Application Priority Data

Mar. 16, 1983 [DE]   Fed. Rep. of Germany ....... 3309310
Aug. 11, 1983 [DE]   Fed. Rep. of Germany ....... 3329026

[51] Int. Cl.$^4$ ............................................. C07D 307/89
[52] U.S. Cl. ..................................... 549/250; 549/251
[58] Field of Search ................................ 549/250, 251

[56] References Cited

U.S. PATENT DOCUMENTS

| | | | |
|---|---|---|---|
| 3,462,461 | 8/1969 | Bloom et al. | 549/251 |
| 4,008,255 | 2/1977 | Wirth et al. | 549/250 |
| 4,145,353 | 3/1979 | Schenk et al. | 549/251 |
| 4,436,922 | 3/1984 | Kita et al. | 549/251 |

*Primary Examiner*—Richard L. Raymond
*Attorney, Agent, or Firm*—Oblon, Fisher, Spivak, McClelland & Maier

[57] ABSTRACT

The invention relates to a process for removing naphthoquinone from phthalic anhydride produced by the air oxidation of naphthalene or mixtures containing naphthalene. Specifically, crude phthalic anhydride containing naphthoquinone is treated at a temperature of 180°–280° C. with an unsaturated aliphatic oil produced by the polymerization of 1,3-dienes and optionally isomerized having a molecular weight of 800–5,000, and optionally in the presence of 1–40 ppm of alkali ions, relative to the crude phthalic anhydride.

9 Claims, No Drawings

PROCESS FOR REMOVING NAPHTHOQUINONE FROM PHTHALIC ANHYDRIDE PRODUCED THROUGH AIR OXIDATION OF NAPHTHALENE

BACKGROUND OF THE INVENTION

1. Field of the Invention

This invention relates to an improved process for the purification of phthalic anhydride produced by air oxidation of naphthalene. More specifically, the undesirable byproduct naphthoquinone is effectively removed from crude phthalic anhydride by treating the crude phthalic anhydride with small quantities of polymeric oils containing several double bonds optionally in the presence of alkali. By this process, phthalic anhydride of higher purity is obtained in higher yields than previously achieved.

2. Description of the Prior Art

Crude phthalic anhydride, which is produced by catalytic air oxidation of naphthalene, contains more than 0.5% by weight of naphthoquinone and other byproducts which are easily separated by distillation, such as maleic anhydride, sulfur and the like. Because naphthoquinone is within the boiling range of phthalic anhydride, its presence diminishes the color and purity of the phthalic anhydride. Therefore, it must be removed prior to distillation. It is highly desireable that the naphthoquinone content in the refined crude product should amount to less than 5 ppm. After distillation the pure phthalic anhydride should have a color value, according to ASTM Standard D1209, of 10 APHA at the most and a naphthoquinone content of 1 ppm at the most. Generally, the removal of the naphthoquinone takes place through conversion to higher condensation products, which then remain behind as a residue after distillation of the crude phthalic anhydride. There are several catalysts that have been recommended for this condensation, but all of them have considerable disadvantages. For example, in U.S. Pat. No. 2,557,499 tin (II) chloride combined with sodium carbonate was suggested. U.S. Pat. No. 2,855,440 recommends a combination of sulfuric acid and boric acid, and U.S. Pat. No. 2,670,325 recommends alkali hydroxide. According to Ullmann's Encyclopaedie der Technischen Chemie, 3d Edition, Vol. 13, p. 72, concentrated sulfuric acid at a temperature of about 200° C. is disclosed as being preferred.

It is known, in practice, that sulfuric acid corrodes the reactor walls under the reaction conditions as well as gives off acidic gases. Furthermore, the neutralization of the sulfuric acid in the crude phthalic anhydride by using calcium carbonate produces inorganic salts which have a highly adverse effect by virtue of their precipitation in the distillation stills and the accompanying inhibition of the distillation. Alkali catalysts, on the other hand, result in the generation of the expected high concentrations of carbon dioxide from the phthalic acid present and in turn, significantly reduce the yield of phthalic anhydride. Attempts to bind the naphthoquinone in the phthalic anhydride to unsaturated natural oils like coconut oil, tung oil, unsaturated natural fatty acids, and the like have been unsuccessful. Only linseed oil lowered the naphthoquinone content to about 5 ppm; however, only strongly colored phthalic anhydride was obtained following vacuum distillation.

SUMMARY OF THE INVENTION

In accordance with the present invention, it has surprisingly been discovered that small quantities of oils containing several double bonds in the molecule can be used to effectively remove naphthoquinone from crude phthalic anhydride.

Further in accordance with the present invention, it has been found that treating crude phthalic anhydride at a temperature of 180°–280° C. with an unsaturated aliphatic oil produced by the polymerization of 1,3-diene having a molecular weight of 800–5,000, preferably 1,003,000 and optionally in the presence of 1–40 ppm, preferably 2–20 ppm, of alkali ions that the effective removal of such impurities as naphthoquinone and maleic anhydride can be achieved.

These and other aspects of the invention will become clear to those skilled in the art upon the reading and understanding of the specification.

DESCRIPTION OF THE PREFERRED EMBODIMENTS

By the process according to the present invention it has surprisingly been possible to obtain a colorless, pure phthalic anhydride with a melting point of 131.2° C., a naphthoquinone content of less than 1 ppm, and a color value of less than 10 APHA. These surprising results have been obtained by heating crude phthalic anhydride produced from naphthalene containing 0.7–0.8% by weight of naphthoquinone and 0.04% by weight of maleic anhydride, for 20 hours with, for example, 0.2% by weight of commercial polybutadiene oils to about 240° C., followed by vacuum distillation. Similar results were obtained with the use of polyisoprene, polydimethylbutadiene, and poly-1,3-pentadiene.

According to another embodiment of the present invention, crude phthalic anhydride was heated for 8 hours to 240° C. with only 0.1% isomerized polyoil (M=1,500) according to, for example, DE-OS No. 29 24 598, DE-OS No. 29 24 577, or E-PS No. 20 924. Following reaction and distillation, the naphthoquinone content was reduced unexpectedly and surprisingly to less than 1 ppm. This result is surprising because, based on the content of 1,3-diene double bonds, assuming a Diels-Alder addition, 20 times as much isomerized polybutadiene oil would have been required to bind the naphthoquinone. The subsequent vacuum distillation produced a color value of less than 10 APHA.

Practically the same results were obtained with the use of isomerized polyoil with a molecular weight of about 3,000, isomerized polyisoprene (M=1,300), and isomeried polypiperylene (M=1,400).

It was further determined that the content of maleic anhydride in the crude phthalic anhydride reduces the effect of the diene polymers. As known, the maleic anhydride can be decomposed with catalytic amounts of alkaline substances (see, for example, Kirk-Othmer, Sec. Ed. Vol. 12, p. 822).

It was surprisingly discovered that the amount of diene polymer may be reduced without problem if a small quantity of alkali ions, for example, in the form of hydroxides, carbonates, bicarbonates, alcoholates, bisulfites, and the like or mixtures thereof are added to the phthalic anhydride melt. These substances may also be dissolved in the polyoil. Sodium, potassium, or lithium compounds are preferred. Best results are obtained if the alkali compound is added with the diene polymer. Since the addition of alkali ions promotes the decomposition of the phthalic anhydride, the amount added should be controlled very carefully to avoid significant losses in yield. The amount of alkali ions added should be sufficient to decompose the maleic anhydride, i.e., about 1–40 ppm relative to the crude phthalic anhydride which amount is significantly smaller than recommended for decomposing naphthoquinone in phthalic anhydride. The reduction of the amount of polydiene is fully effective nevertheless.

Thus the effective removal of naphthoquinone from crude phthalic anhydride is surprisingly achieved by treating crude phthalic anhydride containing naphthoquinone at a temperature of 180°–280° C. with 1.0 to 0.005 weight percent of an unsaturated aliphatic oil produced by the polymerization of 1,3-dienes, with a molecular weight of 800–5,000, preferably 1,000–3,000, optionally in the presence of 1–40 ppm, preferably 2–20 ppm, of alkali ions, relative to the crude phthalic anhydride.

The following non-limiting examples are afforded in order that those skilled in the art may more readily understand the present invention and specified preferred embodiments thereof with respect to the process of the present invention in accordance with the foregoing description.

EXAMPLE 1

500 g of crude phthalic anhydride, produced by naphthalene gas-phase oxidation, contained 0.67% by weight of naphthoquinone (NQ) and 0.04% by weight of maleic anhydride (MA). This sample was melted, mixed with 0.5 g (=0.1%) of polybutadiene with a molecular weight of about 1,500, which through isomerization under the catalytic effect of alkali exhibited 19% of the double bonds in conjugated position, and then heated for 7 hours to 270° C. Following this treatment, the NQ content was less than 5 mg/kg.

COMPARATIVE EXAMPLE 1

370 g of crude phthalic anhydride, produced in the above manner, with 0.66% by weight content of NQ and 0.04% by weight content of MA, was kept for 8 hours at a temperature of 270° C. without additives. Following this treatment, analysis showed an NQ content of 0.04% by weight. Thermal treatment alone had only a slight effect on the NQ content.

EXAMPLE 2

50 g of crude phthalic anhydride containing 0.69% by weight of NQ was treated in test tubes with each of the following additives and heated for 20 hours to 270° C.: polybutadiene (molecular weight about 1,500), polybutadiene (molecular weight about 3,000), polypiperylene (molecular weight about 2,500), polyisoprene (molecular weight about 2,000), isomergin acid from the firm Harburger Fettchemie Brinkmann & Mergell GmbH (conjugated natural fatty acids), coconut oil, and linseed oil. Following treatment, the residual amounts of NQ were determined:

| Additive: | | | | |
|---|---|---|---|---|
| 0.2% polybutadiene | (1,500) | Residual NQ | <5 ppm |
| 0.2% polybutadiene | (2,000) | Residual NQ | <5 ppm |
| 0.3% polypiperylene | (2,500) | Residual NQ | <5 ppm |
| 0.3% polyisoprene | (2,500) | Residual NQ | <5 ppm |
| 0.2% isomergin acid | | Residual NQ | 17 ppm |
| 0.2% coconut oil | | Residual NQ | 0.24% |
| 0.2% linseed oil | | Residual NQ | <5 ppm |

COMPARATIVE EXAMPLE 2

500 g of crude phthalic anhydride, produced by gas-phase oxidation of a naphthalene-xylene mixture, contained 0.32% by weight of NQ and 0.8% by weight of MA. This sample was melted, mixed with 0.5 g (=0.1% by weight) of polybutadiene with a molecular weight of 1,500, which through isomerization exhibited 12% of the double bonds in conjugated position; and heated for 7 hours to 270° C. Following this treatment, the NQ content had been reduced to 25 ppm.

EXAMPLE 3

500 g of crude phthalic anhydride, produced by gas-phase oxidation of a naphthalene-xylene mixture, contained 0.32% by weight of NQ and 0.8% by weight of MA. This sample was melted and heated for 4 hours with 30 ppm anhydrous sodium carbonate to 270° C. Following that it was mixed with 0.5 g of polybutadiene as described in Comparative Example 2 and further heated for 7 hours at the same temperature. The content of NQ was then determined to be 6 ppm.

EXAMPLE 4

500 g of crude phthalic anhydride, produced by gas-phase oxidation of a naphthalene-xylene mixture, contained 0.32% by weight of NQ and 0.8% by weight of MA. This sample was melted and heated for 7 hours with 0.5 g of polybutadiene oil of the above quality and with 30 ppm of anhydrous sodium carbonate to 270° C. The content of NQ was less than 5 ppm.

The following examples illustrate obtaining pure phthalic anhydride through distillation of refined crude phthalic anhydride.

EXAMPLE 5

The crude phthalic anhydride refined as in experiment 1 (NQ content <5 ppm) was distilled at 80 millibars over a ten-day sieve plate column with a reflux ratio of 2:1. The distillation had a melting point of 131.2° C., a color value of <10 APHA, and an NQ content of <1 ppm.

EXAMPLE 6

The crude phthalic anhydrides refined with polybutadiene, polypiperylene, and polyisoprene (Example 2) were distilled under the same conditions as in Example 5. The distillation likewise had a melting point of 131.2° C., a color value of <10 APHA, and an NQ content of <1 ppm.

COMPARATIVE EXAMPLE 3

A crude phthalic anhydride refined with linseed oil (NQ contents = <5 ppm) was distilled under the same conditions as in Example 5. The resulting distillate was strongly colored.

While the invention has been described and illustrated with reference to certain preferred embodiments thereof, those skilled in the art will appreciate that various changes, modifications and substitutions can be made therein without departure from the spirit of the invention. For example, temperature ranges and feed ratios other than the preferred ranges set forth hereinabove may be applicable as a consequence of the nature of various reactants thus employed in the process and such other expected variations or differences in results are contemplated in accordance with the objects and practices of the present invention. It is intended, therefore, that the invention be limited only be the scope of the claims which follow.

What is claimed as new and desired to be secured by Letters Patent of the United States is:

1. A process for the substantial removal of naphthoquinone impurities from crude phthalic anhydride, comprising:

treating a crude phthalic anhydride containing naphthoquinone and other impurities at an elevated temperature with a polymerized 1,3-diene oil selected from the group consisting of polybutadiene, polydimethylbutadiene, poly-1,3-pentadiene, polyisoprene, polypiperylene and mixtures thereof, said polymerized 1,3-diene oil having a molecular weight within the range of about 800 to about 5,000, in an amount sufficient to reduce the content of naphthoquinone to less than 5 ppm.

2. The process according to claim 1, wherein said polymerized 1,3-diene oil is isomerized.

3. The process according to claim 1, wherein the crude phthalic anhydride is further treated in the presence of alkali ions in an amount sufficient to decompose any maleic anhydride present.

4. The process according to claim 3, wherein the amount of alkali ions present is within the range of about 1–40 ppm and the amount of polymerized 1,3-diene oil is within the range of about 1.0 wt. % to about 0,005 wt. %.

5. The process according to claim 4, wherein the amount of alkali ions present is within the range of 2–20 ppm and the amount of polymerized 1,3-diene oil utilized is within the range of about 0.2 to about 0.1 wt. %.

6. The process according to claim 1, wherein the polymerized 1,3-diene oil is polybutadiene and said oil has a molecular weight of about 1,000 to about 3,000.

7. The process according to claim 1 or 2 wherein said treatment is conducted at a temperature within the range of about 180° C. to 280° C.

8. The process according to claim 1 or 2 wherein said treatment is carried out for about 4 hours to 20 hours.

9. The process according to claim 1 or 2 wherein the resulting refined phthalic anhydride is further distilled to reduce the naphthoquinone content to 1 ppm or less.

* * * * *